United States Patent [19]

Fouad

[11] 4,208,405

[45] Jun. 17, 1980

[54] TRACE ELEMENT COMPOSITION FOR IRON DEFICIENCY ANEMIA

[75] Inventor: M. Taher A. Fouad, Layton, Utah

[73] Assignee: Kelatron Pharmaceutical Division of Intermountain Laboratories Inc., Ogden, Utah

[21] Appl. No.: 11,264

[22] Filed: Feb. 12, 1979

Related U.S. Application Data

[63] Continuation-in-part of Ser. No. 859,638, Dec. 12, 1977, which is a continuation-in-part of Ser. No. 761,568, Jan. 24, 1977.

[51] Int. Cl.² .................... A61K 37/00; A61K 33/24
[52] U.S. Cl. .................................... 424/177; 424/131
[58] Field of Search ......................................... 424/177

[56] References Cited

U.S. PATENT DOCUMENTS

| | | | |
|---|---|---|---|
| 1,824,018 | 9/1931 | Horn | 424/177 |
| 2,960,406 | 11/1960 | Cordon | 424/177 |
| 3,440,054 | 4/1969 | Sair | 424/177 |
| 3,463,858 | 8/1969 | Anderson | 424/177 |
| 3,873,296 | 3/1975 | Ashmead et al. | 424/177 |
| 3,969,540 | 7/1976 | Jensen | 426/657 |
| 4,020,158 | 4/1977 | Ashmead et al. | 424/177 |

FOREIGN PATENT DOCUMENTS

2049322  6/1969  France ..................... 424/177

OTHER PUBLICATIONS

How to Better Understand and Apply Results from Feedstuff Analyses.

*Primary Examiner*—Delbert R. Phillips
*Attorney, Agent, or Firm*—H. Ross Workman; J. Winslow Young; Rick D. Nydegger

[57] ABSTRACT

An improved dietary supplement for mammals, the dietary supplement including the essential dietary trace metals, iron, copper and molybdenum. These metals are provided in a highly bioavailable state such as peptide and polypeptide chelates. This invention also includes a method for using natural proteinaceous starting materials for producing the peptide and polypeptide ligands for the chelates. The proteinaceous starting materials are obtained from a primary grown yeast, an isolated vegetable protein, dessicated tissues of animal origin and the like which, upon hydrolysis, yields the peptide and polypeptide ligands suitable for forming chelates with the iron, copper and molybdenum. The metals are each separately chelated with the peptide and polypeptide ligands and thereafter combined in the suitable ratios to form the dietary supplement. The dietary supplement is adsorbed on a suitable food product and provided in an effective amount for consumption in iron deficiency anemia.

5 Claims, No Drawings

TRACE ELEMENT COMPOSITION FOR IRON DEFICIENCY ANEMIA

BACKGROUND

1. Related Application

This is a continuation-in-part of my copending application Ser. No. 859,638 filed Dec. 12, 1977 which is a continuation-in-part of Ser. No. 761,568 filed Jan. 24, 1977.

2. Field of the Invention

This invention relates to dietary supplements and, more particularly to a dietary supplement including the metals iron, copper and molybdenum and its use in iron deficiency anemia.

3. The Prior Art

Although more than 100 elements are known, certain trace elements perform functions which are indispensable to maintaining life. These trace elements are directly involved in the cellular physiochemical reactions and are, therefore, referred to as essential elements. Accordingly, essential elements are those fulfilling certain criteria outlined as follows: (a) the element is present in all healthy tissue of all organisms; (b) its concentration in these healthy tissues is relatively constant; and (c) withdrawal of the element produces similar structural and physiological abnormalities in different species, the abnormalities being prevented or reversed by addition of such elements.

Trace elements fulfilling the above-mentioned properties as essential elements are, in alphabetical order: chromium, cobalt, copper, fluorine, iodine, iron, manganese, molybdenum, nickel, selenium, silicon, tin, vanadium and zinc. Each element exhibits a spectrum of actions that depend, in part, on (a) the amount or dose and (b) the nutritional state of the cell or the recipient regarding that element. The concentration of essential elements is internally controlled by chemical mechanism which tends to restore the correct concentration of these elements thus leading to a normal or symmetrical distribution pattern. Accordingly, increasing amounts of certain elements result in stimulating biological response until a certain plateau is reached. If intake of these elements exceed the foregoing plateau, a pharmacological action followed by toxic effects will appear.

Accordingly, nutritional scientists are continually searching for techniques whereby effective amounts of these essential elements can be safely and efficiently administered to correct ascertained deficiencies in essential elements without imposing undue risks on the recipient.

In view of the foregoing it would be a significant advancement in the art to provide a dietary supplement for mammals wherein the dietary supplement includes at least iron, copper and molybdenum in a form which is readily bioavailable. It would be an even still further advancement in the art to provide a dietary supplement wherein natural proteinaceous starting materials are used for producing the dietary supplement. It would be an even further advancement in the art to provide a dietary supplement in iron deficiency anemia wherein the essential metals are bound to peptides and polypeptides and thereafter adsorbed on a suitable food product. Such an invention is disclosed and claimed herein.

BRIEF SUMMARY AND OBJECTS OF THE INVENTION

The present invention relates to an improved dietary supplement for iron deficiency anemia including a combination of the essential trace elements iron, copper and molybdenum. These essential trace elements are preferably bound to peptides and polypeptides by being chelated with ligands obtained from a hydrolyzed proteinaceous starting material. The proteinaceous starting material is obtained from readily available sources and subjected to a careful hydrolysis to produce suitable ligands acceptable for forming the chelates of this invention. Each of the foregoing essential trace elements are separately chelated and thereafter suitably combined to form the dietary supplement of this invention. The combined chelates are selectively adsorbed on a suitable food product and additional nutritional supplements may also be included with the dietary supplement for iron deficiency anemia.

It is, therefore, a primary object of this invention to provide improvements in dietary supplements for use in iron deficiency anemia.

Another object of this invention is to provide an improved method of preparing a dietary supplement.

Another object of this invention is to provide an improved dietary supplement wherein the essential trace elements of iron, copper and molybdenum are chelated with a suitable chelate substrate and mixed together so as to present the essential trace elements in an advanced state of bioavailability for iron deficiency anemia.

These and other objects and features of the present invention will become more fully apparent from the following description and appended claims.

DETAILED DESCRIPTION OF THE PREFERRED EMBODIMENTS

General

Absorption of essential elements or metals in general is regulated at the intestinal mucosa of the upper portion of the small intestine. Some absorption occurs naturally utilizing the elements in inorganic form. Recent experimental work, however, has determined that these essential metals are more readily and efficiently absorbed and their retention in the body is higher when ingested in the chelated form than similar metals taken in their inorganic forms.

In discussing the metabolism of chelated metals, it is of absolute importance to recognize the functional properties of the trace metal or element in its chelated or complexed form rather than its existence as an inorganic or ionic form. This is particularly important since all vital biological functions can only take place in the former (chelated or complexed) state rather than the latter (inorganic or ionic) form.

The Biological Function of Iron

Although the human body contains only 0.004 percent of this essential trace element, iron plays a central role in all life sustaining processes. In particular, iron, as a main constituent of the respiratory pigment hemoglobin, is essential for the proper functioning of every cell, tissue and organ of the body. Additionally, iron occurs also in proteins that are components of cytochrome C, perioxdase, and many other enzymes. In a normal individual, 70 percent of the iron is present in hemoglobin, 2.5 grams in the blood, 2.4 grams in the red blood cells and only 3.6 milligrams (hereinafter, mg) in the plasma.

Although the red blood corpuscles are continuously undergoing destruction and replacement, where hematin of the hemoglobin is split into an iron compound, bilirubin and other pigment, and the possibility of such released iron to be reused to form hemoglobin, there is always the need for an extrinsic source of iron. Accordingly, this extrinsic source of iron raises the question of iron intake, absorption and metabolism.

Inorganic iron which is ingested is usually complexed to other ingredients present in the food, such as starch, fiber, phosphates, phytate and proteins. Except for the protein portion, iron bound by starch fibers, phytate and phosphates remains unavailable and passes into the feces. Accordingly, iron intake provided by the inorganic iron in such diets may contain several-fold the estimated iron requirement and yet fail to suitably supply the appropriate amount of bioavailable iron needed for children.

The ingested portion of iron ready for absorption follows a complexed and controversial pathway where it is subject to various regulatory mechanisms. For example, ferritin (the primary iron storage protein of the body) is in a dynamic equilibrium with plasma iron. Accordingly, high ferritin levels can regulate iron absorption. Iron absorption is, therefore, generally influenced by the following factors: (1) the level of iron stored in the body, (2) hypoxia and (3) erythropoeitic activity. The foregoing factors affect iron absorption, plus the loss of blood resulting from menstrual bleeding, intestinal lesions, parasites, infections and malignancy are also generally accepted as contributing causes of iron deficiency.

Importantly, two other metals play major roles in iron absorption and metabolism, these are: copper and molybdenum. Accordingly, whenever an iron deficiency is ascertained, consideration must also be given to roles of copper and molybdenum in the absorption and metabolism of iron.

The Biological Function of Copper

Copper constitutes 0.00015 percent of the human body or a total of about 80-100 mg of which 5.6 mg are present in the blood, 3.5 mg in the plasma and 2.2 mg in the red blood cells. Half of the total copper is present in bone and muscle, 10 percent in the liver and lesser amounts in the brain, heart and kidney. The bile is the major pathway for copper excretion, where it is associated with taurochenodroxycholate.

The copper-carrying plasma, ceruloplasmin, has been shown to be a link between copper and iron metabolism. For example it has been demonstrated that the oxidation of ferrous iron is greatly accelerated (10-100 fold) by ceruloplasmin ferroxidase. Like iron, copper is a component of certain enzymes that mediate oxidation-reduction in the mitochondrial electron transfer chain (cytochrome oxidase). In red blood cells, copper is present as erythrocuprein which, unlike plasma copper, is not affected by changes in the dietary supplementation is copper. An increase in serum copper concentration without dietary intake has been reported in myocardial infarction, anemias, leukemias, malignant neoplasia, granulomalous diseases and disseminated lupus erythematosis. Conversely, ceruloplasmin concentration is markedly decreased and followed by the presence of large amounts of copper in the liver and in the brain (Wilson's Disease).

The most important role of ceruloplasmin is its multifunctional enzymatic reactions involved in (1) the oxidation of aromatic diamines and ascorbic acid and (2) mobilization and conversion of liver ferrous iron to ferric iron.

The daily copper requirement for adult humans has been estimated to be approximately 2.5 mg per day with a much higher requirement in early life. For example, the exceptional need for copper in early life is reflected in a daily requirement of about 80 micrograms per kilogram (hereinafter, kg) of body weight, while older children need only about half this amount. Adults require only about 30 micrograms per kg.

The Biological Function of Molybdenum

Approximately 9.3 mg of molybdenum is present in an adult person of which about 19 percent is found in the liver with about 0.083 mg in the blood. The element molybdenum is a component of the intracellular iron-containing enzymes: xanthine oxidase and aldehyde oxidase. The molybdenum present in these enzymes is believed to play an essential role in both iron utilization and cellular metabolism. Accordingly, molybdenum has been established as a dietary factor required for the deposition and maintenance of normal levels of intestinal xanthine oxidase and the activity of aldehyde oxidase which participates in the catalytic action of liver aldehyde oxidase. Like xanthine oxidase, this enzyme, when complexed with molybdenum, possesses remarkable ability in facilitating the interaction with cytochrome C.

It has been shown that a dietary molybdenum deficiency results in a depressed growth rate, and a 25 percent increase in mortality during five-week periods for both rats and chicks. Additionally, a diet adequate in all respects including iron and copper, but lacking molybdenum reduced hemoglobin formation during the first week of life of young chicks to one-third the level seen at hatching. This mortality rate was prevented when as little as 5 ppm molybdenum was added to the diet.

However, excess of either molybdenum or copper will result in anemia by interfering with the absorption and utilization of each other. In addition, there is also evidence that molybdenum, as a component of xanthine oxidase may be necessary for the conversion of ferric-ferritin to ferrous-ferritin, the step immediately preceding the release of iron from ferritin in intestinal mucosal cells or from liver or from hemopoietic storage sites. In the intestinal mucosal cells, xanthine oxidase increases the rate of iron release from the intestinal cellular ferritin, thus participating in the absorption of freshly administered iron intake. Molybdenum-containing enzyme xanthine oxidase also participates in the mobilization of iron from the tissue stores of ferritin. This latter phenomena is of certain clinical importance in mediating iron release under conditions associated with tissue hypoxia.

Additionally, the relative amounts of molybdenum and copper present intracellularly are of vital importance in the mitochondrial oxidation-reduction system where copper is required for cytochrome oxidase activity and molybdenum is needed in the cytochrome reduction. It is, therefore, clear that adequate supplementation with molybdenum in the presence of normal intakes of copper is an absolute necessity for performing these essential reactions vital to all body functions mentioned hereinbefore and the proper metabolism of iron.

Chelating Agents and their Significance on Bioavailability

From the foregoing, it is clear that there is a definite, synergistic interrelationship between the essential elements, iron, copper and molybdenum. Accordingly, attention must now be focused on the combination of these essential elements into a readily bioavailable form. Surprisingly, not only is there a synergistic interrelationship between these essential elements, but they can be made readily bioavailable by binding or chelating them with peptides and polypeptides to form bound essential elements.

Although chelation has been known to both science and industry for many decades, literature and scientific publications on the subject are scanty and it, therefore, becomes readily apparent that basic essential differences in the characteristics of chelating agents have not been duly stressed nor have the implications for use of the chelated minerals in human nutrition been adequately emphasized.

Chelation is the ability of a chelating agent to form a ring with a metal atom. The metal or mineral thus formed is referred to as a chelated mineral. The essential characteristics for all chelating agents is the ability to form a ring with a metal atom under the following conditions: (1) the chelating agent molecule must contain a minimum of two groups which, in turn, combine with the metal atom to form at least one coordinate covalent bond, where the metal is centrally located; (2) donor groups must be available which can coordinate with the central metal atom through their lone electron pair; mainly oxygen, nitrogen (hydroxyl and amino); (3) each of these donor groups must be separated from each other by chains of suitable length to allow the formation of five or six- membered rings; and (4) optimum physical and chemical conditions must be provided to permit the preceding requirements for the completion of the chelation process. Since molybdenum is normally trivalent, it typically complexes with a chelating agent and such a complex will hereinafter be referred to as a chelate for convenience.

Organic acids such as gluconic, fumaric, citric, etc., may form corresponding complexes of gluconates, fumarates, and citrates but do not fulfill the essential requirements as donor groups to form the proper chelate structure. For example, these acids contain oxygen and hydrogen (hydroxyl), but none of their donor groups contain nitrogen (amino), one of the important features required in a chelating agent.

From the foregoing it is clear that an effective and safe chelating agent that meets all of the essential characteristics mentioned hereinbefore, falls into the category for specific types of peptides and polypeptides to form the cyclic or ring metal chelate. Additionally, there are other physical and chemical requirements besides those of chelating agents that influence the process itself in the manufacture of a chemically-defined chelate. These include adequate controls regarding the hydrogen ion concentration, temperature, the peptide and polypeptide linkages or chains of suitable length to permit the formation of required rings of the metal, and a proper stability constant which usually determines the bioavailability of the metal for ionic exchange.

Additional information with respect to the foregoing can be found in my publications: "The Physiochemical Role of Chelated Minerals in Maintaining Optimal Body Biological Functions"; *The International College of Applied Nutrition,* Volume 28, (Summer 1976); and "Chelation and Chelated Minerals"; *The Journal of Applied Nutrition,* Volume 28, No. 1 (Spring 1976).

While the synergistic composition of the present invention may be compounded in an inorganic form, the preferred composition is the chelated mineral form. The protein source for the chelated form of the present invention is obtained from a suitable source such as primary grown yeast, isolated vegetable protein, edible casein or other proteins from animal origin, for example, which are hydrolyzed principally for their peptide and polypeptide components. These protein sources are commercially available and are defined in the Merk Index and other literature well known in the trade. The protein component of these protein sources provides a highly desirable peptide and polypeptide substrate for the chelation process while the resulting product contains other beneficial factors and which are heat resistant and are also most suitable for human consumption. Hydrolysis of the protein source is undertaken under very carefully controlled conditions of pH, temperature, and time. The hydrolysis takes place in solution at an acid pH (0 pH), a temperature range between 80° C. and 90° C. and for a time period of not less than 18 hours and not more than 24 hours.

Another efficient method of hydrolyzing protein is subjecting the protein in solution to an enzymatic process where the pH range is adjusted to 6-8, a temperature range between 50° C. and 60° C., and for a time period of not less than 40 hours and not to exceed more than 48 hours.

The essential metals, iron, copper and molybdenum, are each separately obtained in a suitable inorganic form such as ferrous sulfate, copper carbonate and molybdenum trioxide, for example. The metal salts are each separately solubilized and then each intermixed with discrete portions of the liquid, hydrolyzed protein source. The essential metals are combined with the hydrolyzed protein source on the mole ratio of about 2-4 moles of hydrolyzed protein for each mole of the metal salt added. This mole ratio has been found to provide the appropriate number of metal ions for the number of peptide and polypeptide ligands available for chelation. After being suitably chelated with the hydrolyzed protein, the chelated essential metals are combined in the suitable effective amounts so as to provide the improved dietary supplement of this invention.

The metal chelates are combined in a ratio of about 20-25 parts iron, 2 parts copper and 0.35 parts molybdenum. This ratio is currently believed to represent the most beneficial ratio of these essential elements for a dietary supplement. For an adult, this ratio is reflected in a daily dosage of 20-25 mg iron chelate, 2.0 mg copper chelate and 0.35 mg molybdenum chelate.

The resulting chelates may also be adsorbed or taken up on a suitable food product such as an isolated vegetable protein, primary grown yeast or the like. The product is then dried at 70°-80° C.

The following examples are given by way of illustration to demonstrate the novel process for producing the novel dietary supplement of this invention without, in any way, limiting the scope of the invention.

EXAMPLE I

Water (60 kg) is introduced into a stainless steel, steam-jacketed blender and 40 kg of primary grown yeast is gradually added with mixing. Small additions of hydrochloric acid are made to lower the pH to approximately 0 pH. Mixing of the acidified yeast/water mixture is continued within the blender for about 18-20 hours while maintaining the temperature within about 80°-90° C. The foregoing conditions have been found suitable for adequately hydrolyzing the primary grown yeast to ligands consisting of peptides and polypeptides.

The copper chelate is prepared by removing 10 kg of the hydrolyzed primary grown yeast to a separate vessel and intimately mixing therewith 600 grams of copper carbonate which has been suitably dissolved in dilute hydrochloric acid. After about 30 minutes, the pH of the solution is readjusted to neutrality or slightly above (7.0-7.5 pH) using potassium hydroxide solution.

The molybdenum chelate is prepared by removing 5 kg of the hydrolyzed primary grown yeast to a separate vessel and intimately mixing therewith 92 grams of a molybdenus salt dissolved in concentrated hydrochloric acid. After about 30 minutes, the pH of the solution is readjusted to neutrality or slightly above (7.0-7.5 pH) using a potassium hydroxide solution.

The iron chelate is prepared by adding 16.55 kg ferrous sulfate dissolved in hot water to the remaining hydrolyzed primary grown yeast in the blender. The resultant solution is similarly intimately mixed and held for about 30 minutes before adjusting the pH to neutrality or slightly above (7.0-7.5 pH) by the addition of potassium hydroxide.

The copper chelate and the molybdenum chelates are then added to the iron chelate in the blender and the entire mixture blended for a few minutes to assure intimate mixing of the ingredients. This mixture is held for about 30-60 minutes and then taken up by being adsorbed on a suitable food product such as 22 kg of dry, isolated vegetable protein. The product is then suitably dried at 80°-90° C. The product is a highly bioavailable mixture of iron, copper, and molybdenum chelates having a final ratio of about 20-25 parts iron, 2 parts copper and 0.35 parts molybdenum. These metals are combined with the hydrolyzed primary grown yeast product in a mole ratio of about 2-4 moles hydrolyzed primary grown yeast product for each mole of metal.

EXAMPLE Ia

The dried product obtained from the process of Example I may be further improved by the addition of other nutritional supplements such as vitamins and the like as set forth in the Table, below:

TABLE

| Ingredients for Each 1.0 Gram of Dietary Supplement | |
|---|---|
| Iron (peptide and polypeptide chelate) | 40.00 mg |
| Copper (peptide and polypeptide chelate) | 2.86 mg |
| Molybdenum (peptide and polypeptide chelate) | 0.50 mg |
| Thiamine | 20.00 mg |
| Riboflavin | 20.00 mg |
| Pyridoxine | 20.00 mg |
| Cynocobolomine | 0.06 mg |
| Folic Acid | 5.00 mg |
| Biotin | 1.00 mg |
| Ascorbic Acid | 100.00 mg |

The remainder of the dietary supplement is composed of the isolated vegetable protein upon which the iron, copper and molybdenum chelates are adsorbed. Other suitable ingredients may also be included with the iron, copper and molybdenum chelates, where desired, to produce a final dietary supplement such as intrinsic factor.

EXAMPLE II

The same hydrolysis procedure set forth in Example I was followed by mixing 40 kg of isolated vegetable protein containing 95 percent protein with 160 kg of water. The same conditions of pH, agitation, hydrolysis time and temperature were followed as set forth in Example I to produce the peptide and polypeptides useful for producing the chelates of this invention.

The steps of Example I are also followed to produce the iron, copper and molybdenum chelates of this invention after which they are combined and taken up on 22 kg of a suitable food product such as a primary grown yeast and dried. Additionally, the dried product can be supplemented with other ingredients such as set forth in Example Ia, above.

EXAMPLE III

The same hydrolysis procedure of Example I was followed except that 60 kilograms of water was mixed with 40 kilograms of dessicated liver powder. Acid hydrolysis at the same pH range of approximately 0 was carried out for about 18-20 hours at approximately 70°-75° C. Ligands thus formed include peptides and polypeptides of suitable length for forming iron, copper and molybdenum chelates and chelation is accomplished by adjusting the pH toward neutral as outlined in Example I. After drying, the product thus formed is a highly bioavailable mixture of iron, copper and molybdenum chelates. Said product may be further improved by the addition of other nutritional supplements such as vitamins as set forth in Example Ia.

EXAMPLE IV

The procedure of Example III was again repeated and the wet mixture of chelates is taken up by being adsorbed on 22 kilograms of dry yeast instead of dry isolated vegetable protein. After drying, the product was further improved by the addition of the vitamins mentioned in Example Ia.

EXAMPLE V

Again following the procedure of Example I yeast was used as the source of hydrolyzed protein to provide polypeptides and peptides for the purpose of chelating. The chelates thus formed were then adsorbed on 22 kilograms of dessicated liver added to the mixture of chelated metal. After drying, the product was further improved by the addition of other nutritional supplements such as vitamins as outlined in Example Ia.

EXAMPLE VI

The procedure of Example III was repeated with the exception that 40 kilograms of fresh animal tissues consisting of raw liver, kidneys, spleen and heart were used instead of dessicated liver and the metal chelates were taken up by being adsorbed on 22 kilograms of dry primary grown yeast. After drying, said product was supplemented with ingredients set forth in Example Ia.

EXAMPLE VII

The procedure of Example VI was followed and the metal chelates formed in solution, were taken up by adsorption on 22 kilograms of dry isolated vegetable protein. After drying, the said product was supplemented with nutritional supplements as set forth in Example Ia.

EXAMPLE VIII

The same hydrolysis procedure set forth in Example II was repeated with the exception that 40 kilograms of edible casein instead of the isolated vegetable protein were mixed with 180 kilograms of water. The same conditions of hydrolysis were followed and metal chelates of iron, copper and molybdenum thus formed were taken up by being adsorbed on dry primary grown yeast. Product was then dried and further treated by mixing with other nutritional supplements listed under Example Ia.

EXAMPLE IX

The procedure of Example VIII was repeated with the exception that the metal chelates formed were taken up by being adsorbed on dessicated liver powder instead of the dried primary grown yeast. After drying, the product was supplemented with other nutritional ingredients such as set forth in Example Ia.

EXAMPLE X 1500 grams of U.S.P. ferrous sulfate, 60 grams of U.S.P. copper carbonate, and 9 grams of molybdenum trioxide were blended thoroughly and mixed with the vitamins set forth in Example Ia. The resulting composition was encapsulated in hard shell gelatin capsules. The resulting product was found to provide a synergistic composition for improved iron uptake.

EXAMPLE XI

In a stainless steel, jacketed blender, 150 kilograms of water is heated to 50°-60° C. The following amounts are then added: 18 kilograms of isolated vegetable protein, 18 kilograms of edible casein, 4.0 kilograms of primary grown yeast and 200 grams of a concentrated proteolytic enzyme. The pH of the mixture is adjusted to approximately 6.5-7.5 and the temperature is maintained at 50°-60° C. Mixing of this mixture is continued within the blender for about 40-48 hours at said temperature. Following the technique, the resulting peptides are in short chains providing available number of ligands for proper chelation of copper, molybdenum and iron.

The copper chelate is then prepared by removing 20 kilograms of the hydrolyzed protein mixture to a separate vessel and intimately mixing therewith 750 grams of copper sulfate, which has been suitably dissolved in acidified hot water.

The molybdenum chelate is similarly prepared by removing 7.5 kilograms of the hydrolyzed protein mixture to a separate vessel and intimately mixing therewith 92 grams of molybdenum trioxide dissolved in concentrated hydrochloric acid.

The iron chelate is prepared by adding 16.55 kilograms ferrous sulfate dissolved in acidified hot water to the remaining hydrolyzed protein mixture in the blender. The resultant solution is similarly intimately mixed and held for about 30-60 minutes before taken up by being adsorbed on 22 kilograms of dry, isolated vegetable protein or any similar suitable food product. The mixture is then dried at 80°-90° C. The product is a highly bioavailable mixture of iron, copper and molybdenum chelates having the final ratio of 20-25 parts of iron, 2 parts of copper, and 0.35 parts of molybdenum. These metals are combined with the hydrolyzed protein mixture of isolated vegetable protein, edible casein and yeast in a mole ratio of about 2-4 moles hydrolyzed protein mixture for each one mole of metal.

The dried product thus obtained from the process set forth in the above example, is mixed with other nutritional supplements such as vitamins and alike as set forth in the Table in Example Ia.

The remainder of the dietary supplement is composed of the isolated vegetable protein upon which the iron, copper and molybdenum chelates are adsorbed.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A synergistic dietary supplement composition of matter for iron deficiency anemia consisting of polypeptide bound iron, polypeptide bound copper and polypeptide bound molybdenum in sufficient amounts to improve iron uptake wherein said polypeptides are derived from foodstuff.

2. The synergistic composition defined in claim 1 wherein the polypeptide bound iron, polypeptide bound copper and polypeptide bound molybdenum are adsorbed upon and isolated protein material.

3. The synergistic composition defined in claim 1 wherein the composition is present in ratios of about 20-25 parts iron, 2 parts copper and 0.35 parts molybdenum.

4. A synergistic dietary supplement composition of matter for iron deficiency anemia consisting of iron, copper and molybdenum each bound by polypeptide molecules of primary grown yeast origin and present in ratios of about 20-25 parts iron, 2 parts copper and 0.35 parts molybdenum, the iron, copper and molybdenum polypeptides being adsorbed upon an isolated vegetable protein material.

5. A synergistic dietary supplement for iron deficiency anemia composition of matter consisting of iron, copper and molybdenum each bound by polypeptide molecules of isolated vegetable protein origin and present in ratios of about 20-25 parts iron, 2 parts copper and 0.35 parts molybdenum, the iron, copper and molybdenum polypeptides being adsorbed upon a primary grown yeast material.

* * * * *